US009988542B2

(12) United States Patent
Ozaki et al.

(10) Patent No.: US 9,988,542 B2
(45) Date of Patent: Jun. 5, 2018

(54) TABLET HAVING DRY-INK FILM ON SURFACE THEREOF, AND INK FOR INKJET PRINTER

(71) Applicant: OTSUKA PHARMACEUTICAL CO., LTD., Tokyo (JP)

(72) Inventors: Tomoaki Ozaki, Wakayama (JP); Hidekazu Kitada, Wakayama (JP); Yasuharu Iida, Wakayama (JP); Yoshio Hara, Osaka (JP); Takeshi Matsuda, Osaka (JP); Tadashi Mukai, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days. days.

(21) Appl. No.: 14/414,714

(22) PCT Filed: Jul. 17, 2013

(86) PCT No.: PCT/JP2013/069377
§ 371 (c)(1),
(2) Date: Jan. 14, 2015

(87) PCT Pub. No.: WO2014/014010
PCT Pub. Date: Jan. 23, 2014

(65) Prior Publication Data
US 2015/0203698 A1 Jul. 23, 2015

(30) Foreign Application Priority Data

Jul. 20, 2012 (JP) .................................. 2012-161583

(51) Int. Cl.
*C09D 11/322* (2014.01)
*B41M 5/00* (2006.01)
(Continued)

(52) U.S. Cl.
CPC ............. *C09D 11/322* (2013.01); *A61J 3/007* (2013.01); *A61K 9/2072* (2013.01); *B41M 5/0047* (2013.01); *B41M 5/0088* (2013.01); *C09D 11/08* (2013.01); *C09D 11/324* (2013.01); *A61K 47/02* (2013.01); *A61K 47/44* (2013.01)

(58) Field of Classification Search
None
See application file for complete search history.

(56) References Cited

U.S. PATENT DOCUMENTS 4,548,825 A 10/1985 Voss et al.
2011/0128557 A1 6/2011 Kinoshita et al.

FOREIGN PATENT DOCUMENTS

CN 102231990 A 11/2011
EP 1 849 840 A1 10/2007
(Continued)

OTHER PUBLICATIONS

Machine translation, JP 2010-248313 A (2010).*
(Continued)

*Primary Examiner* — Bethany P Barham
*Assistant Examiner* — Barbara S Frazier
(74) *Attorney, Agent, or Firm* — Sughrue Mion, PLLC

(57) ABSTRACT

The invention provides a tablet having a powdered or soft surface on which a dry-ink film of information for improving identifiability of the tablet is printed, and provides an ink for inkjet printers.

4 Claims, 5 Drawing Sheets

(51) Int. Cl.
*C09D 11/08* (2006.01)
*A61J 3/00* (2006.01)
*A61K 9/20* (2006.01)
*C09D 11/324* (2014.01)
*A61K 47/02* (2006.01)
*A61K 47/44* (2017.01)

(56) References Cited

FOREIGN PATENT DOCUMENTS

| JP | 52-146307 A | 12/1977 |
|---|---|---|
| JP | 57-001768 A | 1/1982 |
| JP | 01-178564 A | 7/1989 |
| JP | 07-081050 A | 3/1995 |
| JP | 2000-042089 A | 2/2000 |
| JP | 2000-507820 A | 6/2000 |
| JP | 2000-512303 A | 9/2000 |
| JP | 2005-531330 A | 10/2005 |
| JP | 2008-48924 A | 3/2008 |
| JP | 2010-248313 A | 11/2010 |
| JP | 201251114 A | 3/2012 |
| TW | 200836773 A | 9/2008 |
| WO | 97/35933 A1 | 10/1997 |
| WO | 97/48384 A2 | 12/1997 |
| WO | 2004/003089 A1 | 1/2004 |
| WO | 2008089087 A2 | 7/2008 |
| WO | 2009/025371 A1 | 2/2009 |
| WO | 2010019239 A2 | 2/2010 |

OTHER PUBLICATIONS

International Search Report for PCT/JP2013/069377 dated Oct. 15, 2013.
Supplementary European Search Report dated Jan. 25, 2016 from the European Patent Office in counterpart EP Application No. 13819445.1.
Office Action dated Jan. 5, 2017, issued for the corresponding European patent application No. 13819445.1.

* cited by examiner

TABLET HAVING DRY-INK FILM ON SURFACE THEREOF, AND INK FOR INKJET PRINTER

CROSS REFERENCE TO RELATED APPLICATIONS

This application is a National Stage of International Application No. PCT/JP2013/069377 filed Jul. 17, 2013, claiming priority based on Japanese Patent Application No. 2012-161583 filed Jul. 20, 2012, the contents of all of which are incorporated herein by reference in their entirety.

TECHNICAL FIELD

The present invention relates to a tablet that has a dry-ink film on its surface and to ink for inkjet printers.

BACKGROUND ART

Since many preparations, such as tablets, have similar shapes, they are not easily identified once removed from press-through packages or wrapping containers. Some tablets have punch marks on their surfaces, but these marks are not helpful to identify the types of tablets. Therefore, there is a possibility of choosing the wrong tablet, which may result in medical malpractice. Medicine users and pharmacists have therefore demanded drug names or symbols be printed on the tablet surfaces for clear identification.

As a means for solving such a problem, printing characters or the like on the surface of a preparation has been known for identifying the preparation. Examples of such printed preparations include film-coated tablets and capsules. Contact offset printing is generally used for printing on these preparations (film-coated tablets or capsules).

However, when contact offset printing is performed on soft tablets that have a surface with a small strength, such as uncoated tablets, in particular, orally disintegrating tablets, the contact surface with the tablet may be smudged because of its easy disintegration or the powder generated on the surface. Therefore, it has been difficult to perform contact offset printing on soft tablets such as uncoated tablets.

Performing contactless printing on tablets by using an inkjet printer or the like is also known.

For example, Patent Document 1 discloses a technique involving an inkjet printer for printing characters or marks on molded drug products. Examples of objects to be printed on include tablets, coated tablets, capsules, and suppositories. As the components of the colorant liquid, Patent Document 1 discloses solvent components such as alcohol, water, lower aliphatic alcohol, glycol, glycerol, and the like; and adhesive components such as methylcellulose, hydroxypropylmethyl cellulose, hydroxypropylmethyl cellulose phthalate, and the like.

Further, Patent Document 2 discloses printing on tablets by using a continuous inkjet printer.

Further, Patent Document 3 discloses a formulation of ink for continuous inkjet printing containing titanium oxide and aluminum lake, which is a food dye (an edible dye).

Further, Patent Document 4 discloses laser imprinting and inkjet printing as a method for printing marks on rapidly disintegrating dosage forms. Patent Document 4 discloses a dosage form that disintegrates within one or two seconds in the mouth as one example of rapidly disintegrating dosage forms. Patent Document 4 discloses that although only marking on impermeable articles was possible in the past, the method of Patent Document 4 enables marking on porous solid dosage forms. Patent Document 4 further discloses that a mixed system of water and alcohol may be used as ink.

Patent Document 5 discloses an inkjet ink that contains an oil or wax, and can be used for marking on tablets.

Patent Document 6 discloses a coating method using an inkjet method. This method is intended to increase the strength of the drug, and the object of the method differs from techniques for printing marks on easily disintegrating tablets.

Patent Document 7 is directed to printing on tablets by using an inkjet method, and discloses an apparatus that can be suitably used for uncoated tablets, in particular, orally disintegrating tablets. Patent Document 7 discloses that the suitable void ratio of the tablet is preferably 5 to 40% or less, further preferably 5 to 30%. Patent Document 7 is also directed to multicolor printing and discloses a drop-on-demand printer using a piezo element. Patent Document 7 discloses molded tablets, wet tablets, compressed tablets, etc., as target tablets.

Further, Patent Document 8 discloses printable and edible ink for inkjet printers. Patent Document 8 discloses that the ink contains a carbon powder pigment, shellac, a cellulose-based resin, ethanol, and water, and that the ink can be used for printing on food and also on tablets.

CITATION LIST

Patent Documents

Patent Document 1: JPS57-1768A
Patent Document 2: JPH07-81050A
Patent Document 3: JP2000-507820A
Patent Document 4: JP2000-512303A
Patent Document 5: JP2005-531330A
Patent Document 6: JP2008-48924A
Patent Document 7: International Publication WO 2009/025371
Patent Document 8: JP2010-248313A

SUMMARY OF INVENTION

Technical Problem

However, in Patent Document 1, the tablets to be printed on are coated tablets. Therefore, Patent Document 1 merely discloses an aqueous solution and an isopropanol solution of a colorant, and a dispersion of iron oxide in glycol.

Further, Patent Document 2 does not have a detailed description regarding the characteristics of the tablets or the composition of the ink.

In Patent Document 3, the invention is mainly used for food and does not specifically ensure adequacy with respect to easily disintegrating tablets.

Although Patent Document 4 mentions marking on easily disintegrating preparations, it nowhere specifically discloses inkjet ink or details of printed tablets, and merely discloses a technique of easy disintegration.

In Patent Document 5, suitability for easily disintegrating tablets is not considered, and thus there are problems regarding adherence on the surface of the easily disintegrating tablets or transfer of the ink onto another tablet by friction between the tablets.

Patent Document 6 is directed to a coating method using an inkjet method, and the method is intended to increase the strength of the drug; thus, the object of the method differs from techniques for printing marks on easily disintegrating tablets.

Patent Document 7 discloses specific void ratios of the tablets; however, Patent Document 7 merely describes a food dye (an edible dye), a water-soluble solvent, and purified water, and nowhere describes ink in detail.

The ink for inkjet printers disclosed in Patent Document 8 can be suitably used for forming a dry-ink film on a preparation that has a hard surface such as a film-coated tablet or a capsule because the dry-ink film formed by this ink does not easily peel off.

However, if this inkjet printing is performed on an easily disintegrating tablet with a surface on which powder is attached, the dry-ink film becomes detached from the surface of the tablet (see FIG. 1) or the dry-ink film transfers from the surface of a tablet onto another tablet (see FIG. 2) when the printed tablets are brought into contact with each other. As a result, the part of the dry-ink film attached to the tablet may look like foreign matter or a smudge.

Thus, easily disintegrating tablets frequently have problems such as printed characters disappearing due to the dry-ink film becoming detaching from the tablet surface, and the generation of adhered substances caused by the dry-ink film becoming detached from the tablet surface, which, at a glance, looks like foreign matter or a smudge.

A means for solving such problems may be a method of preventing easy detachment of the printed ink. More specifically, it is possible to use a method of increasing the resin content in the ink formulation, thereby increasing the strength for fixing the pigment of the ink. For example, in the invention of Patent Document 8, it is possible to adjust the resin content of the ink. However, by simply increasing the resin content, the viscosity of the ink increases, thereby worsening the adequate viscosity for the inkjet printer. Therefore, the stability of the ink decreases (ink discharge becoming unstable due to the increase in viscosity), thereby causing problems such as decreased printability (see FIG. 3).

In order to solve the above problems of the known methods, an object of the present invention is to provide a tablet that has a soft or powdery surface on which is printed a dry-ink film of information for improving identification of the tablet, and to provide an ink for inkjet printer.

Solution to Problem

The inventors of the present invention conducted extensive research to solve the above problems and found that by printing on the surface of a specific tablet by using a contactless inkjet printing method with an ink for inkjet printers that has a specified ink film hardness on a dry basis, it is possible to reduce detachment of the dry-ink film from the surface of the tablet, and limit the transfer and adherence of the printed characters onto another tablet, or, even if transfer or adherence occurs, it can be reduced to an allowable extent. Based on this finding, the inventors have completed the present invention.

Specifically, the present invention relates to the following tablets, which have a dry-ink film on the surface, and to ink for inkjet printers.

Item 1. A tablet having a surface printed with an ink having a pencil hardness of 2B to 4H with respect to a dry-ink film formed after the ink is dried, the amount of powder in the surface of the tablet being 0.2 wt % or less based on the total weight of the tablet.

Item 2. The tablet according to Item 1, wherein the dry-ink film has a reflection density of 0.1 to 0.3.

Item 3. The tablet according to Item 1 or 2, wherein the tablet is an uncoated tablet.

Item 4. The tablet according to any one of Items 1 to 3, wherein the dry film contains a resin and a pigment, the amount of the resin being 15 to 50 parts by weight per part by weight of the pigment.

Item 5. The tablet according to Item 4, wherein the resin contains shellac.

Item 6. The tablet according to Item 4 or 5, wherein the pigment contains a carbon powder pigment.

Item 7. The tablet according to any one of Items 1 to 6, wherein the dry film is a dry-ink film printed by using an inkjet printer.

Item 8. The tablet according to any one of Items 1 to 7, wherein the tablet is an orally disintegrating tablet.

Item 9. An ink for inkjet printers for printing on a surface of a tablet, the surface of the tablet having 0.2 wt % or less of powder based on the total weight of the tablet, the ink having a pencil hardness of 2B to 4H with respect to a dry film formed after the ink is dried.

Item 10. The ink for inkjet printer according to Item 9, wherein the dry film formed after the ink is dried has a reflection density of 0.1 to 0.3.

Item 11. The ink for inkjet printers according to Item 9 or 10, wherein the ink contains a resin and a pigment, the amount of the resin being 15 to 50 parts by weight per part by weight of the pigment.

Item 12. The ink for inkjet printers according to Item 11, wherein the ink containing 0.05 to 0.7 wt % of the pigment, 0.75 to 25 wt % of the resin, and 50 to 98 wt % of ethanol.

Item 13. The ink for inkjet printers according to Item 11 or 12, wherein the pigment contains a carbon powder pigment.

Item 14. The ink for inkjet printers according to any one of Items 11 to 13, wherein the resin contains shellac.

Item 15. An ink for inkjet printers containing a resin and a pigment, the amount of the resin being 15 to 50 parts by weight per part by weight of the pigment, the resin containing shellac, the pigment containing a carbon powder pigment, a dry film formed after the ink is dried having a pencil hardness of 2B to 4H, the dry film having a reflection density of 0.1 to 0.3.

Item 16. The ink for inkjet printers according to Item 15, wherein the ink containing 0.05 to 0.7 wt % of the pigment, 0.75 to 25 wt % of the resin, and 50 to 98 wt % of ethanol.

Item 17. A process for producing a tablet having a dry-ink film, comprising the step of printing with an ink for inkjet printers having a pencil hardness of 2B to 4H with respect to a dry film formed after the ink is dried on a surface of a tablet using an inkjet printer, the surface of the tablet having 0.2 wt % or less of powder based on the total weight of the tablet.

Item 18. The process according to Item 17, wherein the dry-ink film has a reflection density of 0.1 to 0.3.

Item 19. The process according to Item 17 or 18, wherein the ink for inkjet printers contains a resin and a pigment, the amount of the resin being 15 to 50 parts by weight per part by weight of the pigment.

Item 20. The process according to any one of Items 17 to 19, wherein the tablet is an uncoated tablet.

Item 21. The process according to any one of Items 17 to 20, wherein the tablet is an orally disintegrating tablet.

Item 22. A process for printing with an ink for inkjet printers containing a resin and a pigment on a surface of a tablet having 0.2 wt % or less of powder based on the total weight of the tablet using an inkjet printer, the amount of the resin in the ink for inkjet printers being 15 to 50 parts by weight per part by weight of the pigment.

Item 23. A tablet having a surface with a dry film of an ink containing a resin and a pigment, the surface of the tablet having 0.2 wt % or less of powder based on the total weight of the tablet, the amount of the resin in the dry film being 15 to 50 parts by weight per part by weight of the pigment.

Item 24. The tablet according to Item 23, wherein the tablet has a surface hardness of 5 to 20 g.

Item 25. The tablet according to Item 24, wherein the entire dry-ink film contains 1.2 to 6 wt % of the pigment and 70 to 90 wt % of the resin.

Item 26. The tablet according to Item 24 or 25, wherein the resin contains shellac.

Item 27. The tablet according to any one of Items 24 to 26, wherein the resin contains 90 wt % or more of shellac.

Item 28. The tablet according to any one of Items 24 to 27, wherein the pigment contains a carbon powder pigment.

Item 29. An ink for inkjet printers containing a resin and a pigment for printing on a surface of a tablet having 0.2 wt % or less of powder based on the total weight of the tablet, the amount of the resin being 15 to 50 parts by weight per part by weight of the pigment.

Item 30. The ink for inkjet printers according to Item 29, wherein the tablet has a surface hardness of 5 to 20 g.

Item 31. The ink for inkjet printers according to Item 29 or 30, wherein the ink containing 0.05 to 0.7 wt % of the pigment, 0.75 to 25 wt % of the resin, and 50 to 98 wt % of ethanol.

Item 32. The ink for inkjet printers according to any one of Items 29 to 31, wherein the resin contains shellac.

Item 33. The ink for inkjet printers according to any one of Items 29 to 32, wherein the resin contains 90 wt % or more of shellac.

Item 34. The ink for inkjet printers according to any one of Items 29 to 33, wherein the pigment contains a carbon powder pigment.

Advantageous Effects of Invention

The ink for inkjet printing of the present invention ensures superior printability, and, in particular, enables adjustment in hardness of the dry-ink film formed after the ink is dried. Therefore, the ink for inkjet printing of the present invention enables printing on a film-coated tablet with a hard surface, as well as a tablet with a soft surface such as an uncoated tablet. In particular, when printing is performed on a tablet with a soft surface such as an uncoated tablet, an even greater effect is ensured by specifying the amount of powder on the tablet surface to 0.2 wt % or less based on the total weight of the tablet.

Further, a tablet having a surface printed with the above ink for inkjet printing ensures superior adhesiveness between the tablet surface and the dry-ink film, and so the dry-ink film does not easily become detached. Therefore, it is possible to avoid the disappearance of the dry-ink film, or the transfer or adherence of the dry-ink film to another tablet, thereby providing an effect of eliminating generation of tablets which, at a glance, appear to be contaminated with foreign matter or have smudges.

DESCRIPTION OF EMBODIMENTS

1. Tablet Having a Dry-ink Film

Figure 1:
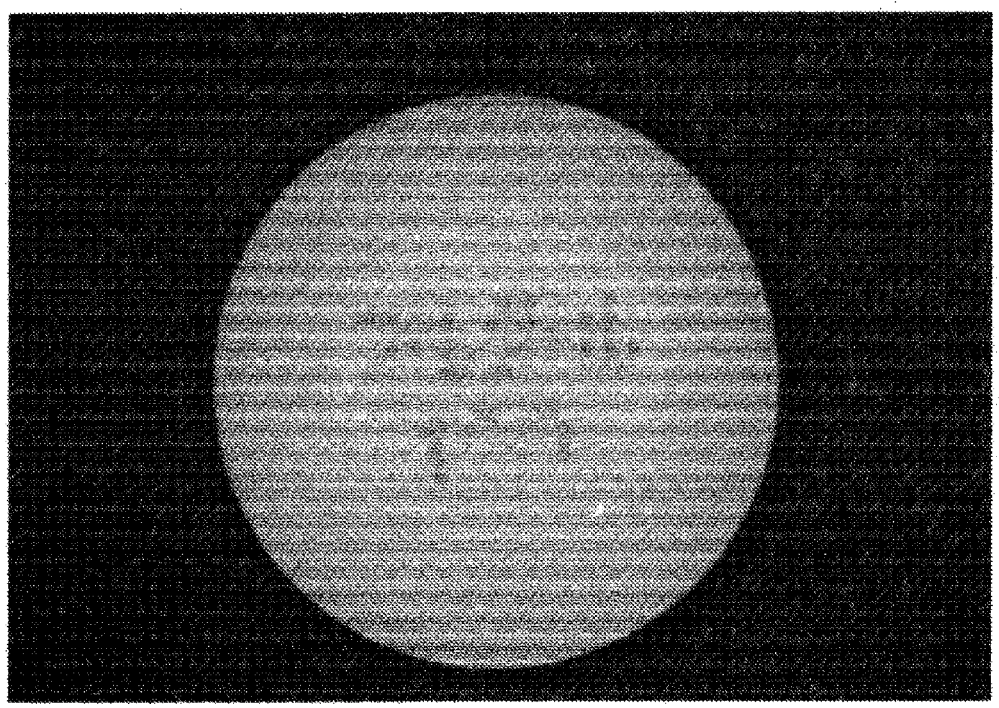
FIG. 1 shows a photo of a tablet with a detached dry-ink film due to contact between the printed tablets when the tablet surfaces are printed on by using a known inkjet printing method.
Figure 2:
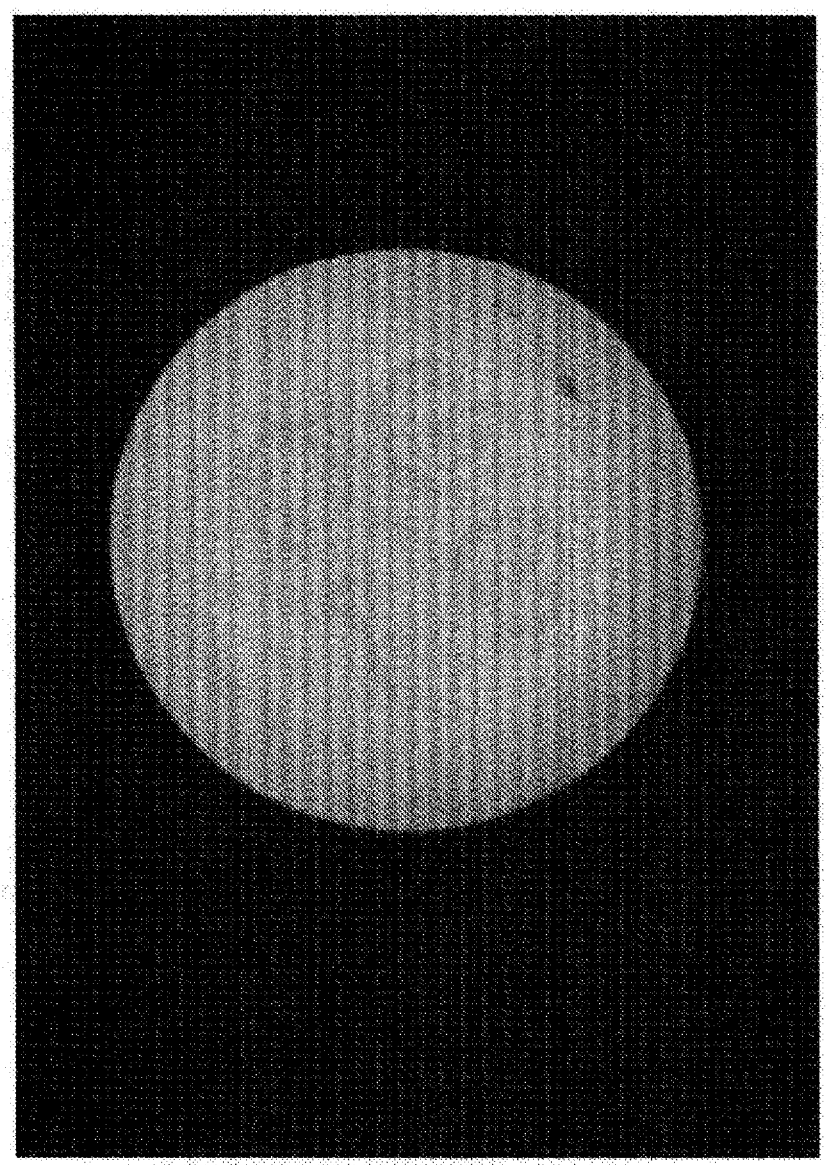
FIG. 2 shows a photo showing a state in which a dry-ink film is transferred onto another tablet due to contact between the printed tablets when the tablet surfaces are printed on by using a known inkjet printing method.
Figure 3:
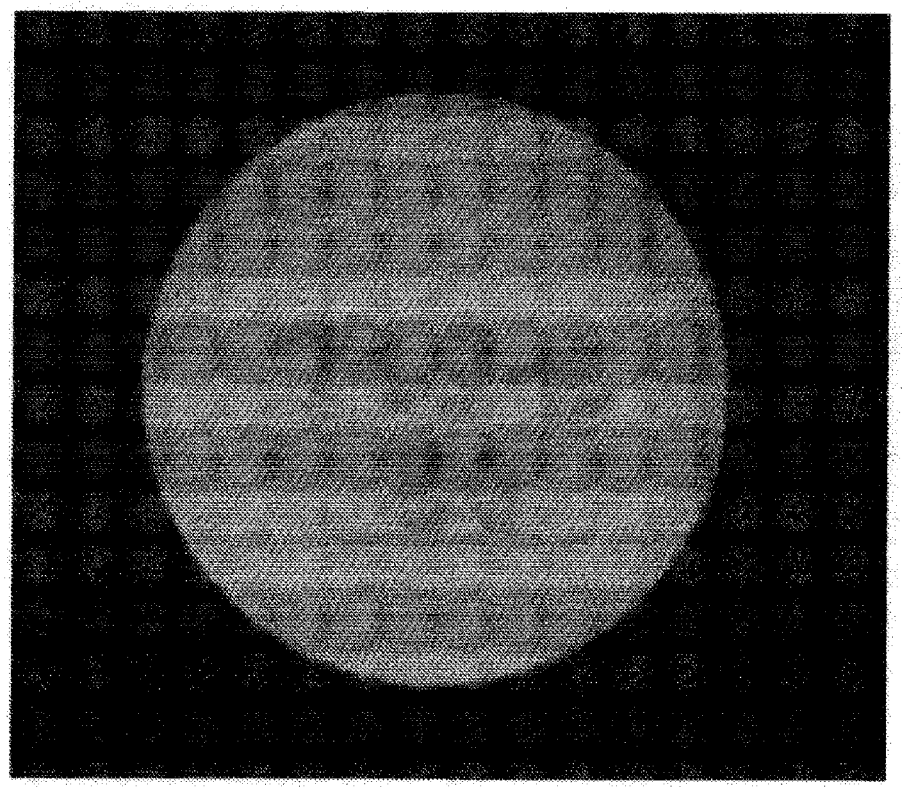
FIG. 3 shows a photo of an insufficiently printed tablet due to a decrease in printability when the tablet is printed on by using a known method.

The tablet having a dry-ink film of the present invention has, on its surface, a dry-ink film printed with ink for inkjet printers.

The amount of the powder derived from the tablet component in the tablet surface to be printed on is preferably as small as possible so as to prevent the dry-ink film from becoming detached from the surface or the dry-ink film from transferring to another tablet by contact. More specifically, the amount of the powder in the tablet surface is preferably 0.2 wt % or less, more preferably 0.1 wt % or less, further preferably 0.06 wt % or less, based on the total weight of the tablet. A tablet such as this, with a surface containing a small amount of powder can be obtained, for example, by using a method of placing a tablet on a 30-cm sieve and removing powder from the tablet with a vacuum cleaner while mildly vibrating the tablet. This method can reduce the powder content to about 0.05 wt %.

The tablet to be printed on with the ink for inkjet printing of the present invention is not particularly limited insofar as the tablet has a surface containing 0.2 wt % or less of powder. Example of such tablets include various types of tablets ranging from tablets with a hard surface such as film-coated tablets to tablets with a soft surface such as uncoated tablets. In particular, by specifying the amount of the powder in the tablet surface to 0.2 wt % or less, good effects are obtained with regard to legibility, detachment, transfer or the like of the ink when printing is performed on a tablet with a soft surface, such as an uncoated tablet, using the ink of the present invention, which is specified to have a pencil hardness of 2B to 4H with respect to a dry-ink film.

The hardness of the tablet of the present invention is generally 5 to 300 g based on the surface hardness. The hardness can vary; a softer tablet has a hardness of 5 to 100 g, an even softer tablet has a hardness of 5 to 50 g, and still further softer tablet has a hardness of 5 to 20 g. The tablet having a dry-ink film of the present invention can be obtained even from such a tablet with a soft surface, e.g., a tablet with a surface hardness of 5 to 100 g (more preferably 5 to 50 g, and further preferably 5 to 20 g) by using ink for inkjet printers. The surface hardness of the tablet may be measured according to the JIS R 3255 scratch test using a continuous loading surface measurement device and a sapphire indenter (R=0.1 mm), at a movement rate of 0.1 mm/s.

The tablet described above is not particularly limited. Examples include various tablets ranging from tablets with a hard surface such as film-coated tablets to tablets with a soft surface such as uncoated tablets (bare tablets) including orally disintegrating tablets (OD tablets). In terms of surface hardness, the tablets have a surface hardness of, for example, 5 to 300 g. The components of the tablets are not particularly limited, but the components are generally as follows.

The tablet contains a pharmacologically active substance, and additives such as an excipient, a binder, a disintegrant, a fluidizer, a lubricant, and the like.

The pharmacologically active substance to be incorporated into tablets is not particularly limited, and many known pharmacologically active substances may be used. Examples include general pharmacologically active substances to be incorporated into preparations for respiratory organs, preparations for digestive systems, preparations for circulatory organs, preparations for central nerves, preparations for peripheral nerves, antibiotics, chemotherapeutic agents, anti-tumor agents, platelet aggregation inhibitors, anti-allergy agents, vitamins, and the like.

Examples of pharmacologically active substances include cilostazol, aripiprazole, 7-[4-(4-benzo[b]thiophen-4-yl-piperazin-1-yl) butoxy]-1H-quinoline-2-one, delamanid, 5-aminosalicylic acid, acyclovir, aspirin, acetylsalicylic acid, acetaminophen, ampicillin, isoniazid, ibuprofen, indometacin, escitalopram, ethenzamide, enalapril, erythromycin, omeprazole, glimepiride, grepafloxacin, ketoconazole, conivaptan, satavaptan, salbutamol, salazosulfapyridine, salazopyrin, diazepam, diclofenac, diclofenac sodium, dipyridamole, cimetidine, simvastatin, sucralfate, sulpiride, sulfasalazine, celecoxib, tacrolimus, theophylline, tegafur, dexamethasone, dextromethorphan, tetomilast, terfenadine, doxorubicin, triamcinolone, tolvaptan, nadifloxacin, naproxen, nifedipine, urea, sodium valproate, haloperidol, valacyclovir, paliperidone, hydrocortisone, pioglitazone, famotidine, phenacetin, phenytoin, phenylpropanolamine, budesonide, pravastatin, pravastatin sodium, fluorouracil, prednisolone, prednisone, furosemide, probucol, vesnarinone, penicillin, perphenazine, voglibose, chlorpheniramine maleate, midazolam, doxazosin mesilate, methotrexate, morphine, ranitidine, lansoprazole, lisinopril, risperidone, lidocaine, rivoglitazone, rebamipide, levodopa, rotigotine, lovastatin, lorazepam, warfarin, ambroxol hydrochloride, carteolol hydrochloride, diphenhydramine hydrochloride, tamsulosin hydrochloride, nicardipine hydrochloride, hydralazine hydrochloride, pioglitazone hydrochloride, buprenorphine hydrochloride, procaterol hydrochloride, mozavaptan hydrochloride, ranitidine hydrochloride, levocarnitine hydrochloride, cortisone acetate, and salbutamol sulfate. Cilostazol, tolvaptan, rebamipide, procaterol hydrochloride, aripiprazole, and theophylline are preferable.

Examples of these pharmacologically active substances include a free body, a salt, and a solvate (hydrate, ethanolates, etc.), and a crystalline polymorphism. The pharmacologically active substance may be crystalline or amorphous. Further, the pharmacologically active substance may be water-soluble or lipid-soluble, and may be poorly soluble in water.

The content of the pharmacologically active substance in the tablet is generally about 0.01 to 80 wt %, preferably about 0.1 to 70 wt %, more preferably about 1 to 50 wt %.

The excipients may be selected from a wide range of known excipients. Examples include sugars such as sucrose, lactitol, trehalose, maltose, lactose, saccharose, glucose, palatinit, palatinose, isomaltooligosaccharide, fructose, maltose, refined sugar, or lactose; sugar alcohols such as mannitol, sorbitol, maltitol, erythritol, or xylitol; starches such as corn starch or potato starch; pharmaceutically acceptable inorganic acid compounds containing one or more of aluminum, magnesium and calcium such as magnesium aluminometasilicate, magnesium aluminosilicate, calcium hydrogen-phosphate, anhydrous calcium hydrogen-phosphate, anhydrous calcium hydrogen-phosphate agglomerated substance, hydrotalcite, aluminum silicate, calcium phosphate, calcium carbonate, calcium silicate, magnesium silicate, magnesium oxide, magnesium hydroxide, alumina magnesium hydroxide, aluminum hydroxide dried gel, or magnesium carbonate; cellulose such as crystalline cellulose, carboxymethyl cellulose, ethyl cellulose, carboxymethylethyl cellulose, carmellose sodium, hydroxyethyl cellulose, hydroxyethylmethyl cellulose, hydroxypropyl cellulose, or hydroxypropylmethyl cellulose; starches such as corn starch, rice starch, potato starch, wheat-flour starch, partly pregelatinized starch, hydroxypropyl starch, sodium carboxymethyl starch, or dextrin; aminoalkylmethacrylate copolymer RS; polyethyleneglycol (macrogol) (e.g., polyethylene glycol 6000, polyethylene glycol 4000, etc.); and polyvinyl alcohol. These excipients may be used solely or in a combination of two or more.

The content of the excipient in the tablet is generally about 0.1 to 70 wt %, preferably about 1 to 60 wt %, more preferably about 5 to 50 wt %.

The binders may be selected from a wide range of known binders. Examples include methyl cellulose, ethyl cellulose, hydroxypropyl cellulose, hydroxypropylmethyl cellulose, polyvinyl pyrrolidone, gelatin, agar, gum arabic, powdered gum arabic, polyvinyl alcohol, dextrin, pullulan, aminoalkylmethacrylate copolymer RS, and macrogol (for example, polyethylene glycol 6000 and polyethylene glycol 4000). These binders may be used solely or in a combination of two or more.

The content of the binder in the tablet is generally about 0.1 to 50 wt %, preferably about 1 to 40 wt %, more preferably about 5 to 30 wt %.

Examples of disintegrants include low-substituted hydroxypropylcellulose, sodium carboxymethyl starch, carmellose, sodium croscarmellose, carboxymethyl cellulose, crystalline cellulose, and crospovidone. These disintegrants may be used solely or in a combination of two or more.

The content of the disintegrant in the tablet is generally about 0.1 to 15 wt %, preferably about 0.5 to 10 wt %, more preferably about 1 to 7.5 wt %.

Examples of fluidizers include hydrated silicon dioxide, light anhydrous silicic acid, heavy anhydrous silicic acid, and titanium oxide. The contents of these fluidizers are according to general amounts of fluidizers to be incorporated into tablets.

Examples of lubricants include metal stearate, such as stearic acid, polyoxyl stearate, magnesium stearate, calcium stearate; sodium stearyl fumarate, talc, colloidal silica, sucrose fatty acid ester, hydrogenated oil, dimethylpolysiloxane, and polyethyleneglycols. These lubricants may be used solely or in a combination of two or more.

The content of the lubricant in the tablet is generally about 0.01 to 1 wt %, preferably about 0.1 to 0.6 wt %.

In addition to the above additives (excipients, binders, disintegrants, fluidizers, and lubricants), various preparation carriers such as pH adjusters, absorbefacients, taste-collecting agents, sweetening agents, coloring agents, or flavors may be used. The contents of these preparation carriers are according to general amounts of preparation carriers to be incorporated into tablets.

Examples of sweetening agents include acesulfame potassium, aspartame, saccharin or a salt thereof, sweet tea, sweetroot powder, glycerin, glycyrrhizic acid or a salt thereof, stevia or a salt thereof, sucralose, thaumatin, honey, and starch syrup.

Examples of taste-collecting agents include ascorbic acid or a salt thereof, glycine, sodium chloride, magnesium chloride, hydrochloric acid, diluted hydrochloric acid, citric acid or a salt thereof, anhydrous citric acid, L-glutamic acid or a salt thereof, succinic acid or a salt thereof, acetic acid, tartaric acid or a salt thereof, sodium hydrogencarbonate, fumaric acid or a salt thereof, malic acid or a salt thereof, glacial acetic acid, disodium inosinate, honey, and erythritol.

Examples of flavors include various items referred to as "flavoring agents," such as orange essence, orange oil, caramel, camphor, cinnamon oil, spearmint oil, strawberry essence, chocolate essence, cherry flavor, spruce oil, pine oil, peppermint oil, vanilla flavor, bitter essence, fruit flavor, peppermint essence, mix flavor, mint flavor, menthol, lemon powder, lemon oil, or rose oil.

Examples of coloring agents include food dyes (edible dyes) such as Food Red No. 3, Food Yellow No. 5, or Food Blue No. 1; yellow iron sesquioxide; iron sesquioxide; brown iron oxide; black iron oxide; copper chlorophyll; sodium copper chlorophyllin; riboflavin; green tea powder; and tar dye.

The tablet of the present invention may be produced by mixing the components described above by using a known method. For example, the tablet may be produced either directly by using a tabletting method, or by using a method of producing granules using a dry granulation method or a wet granulation method, and then making tablets by using a tabletting method. Specifically, the production method includes a mixing step and a tabletting step. As required, a dry granulation step, a wet granulation step, a drying step, a particle size regulation step, etc., may be performed before or after the mixing step and the tabletting step. The tablet is produced using a versatile device generally used in the field of pharmaceuticals.

The pressure applied from a tablet machine when the tablet is compression-molded is, for example, about 200 to 600 kg/pestle.

By specifying the pressure to this range, the tablet hardness will not be decreased, thereby ensuring sufficient hardness in handling tablets, and ensuring sufficiently easy disintegration.

The diameter or the major axis of the tablet is preferably in a range of about 3 to 30 mm in terms of productivity, easy handling, and easy administration. Further, when the pharmaceutical solid preparation of the present invention is produced as a granular agent, the particle diameter of the granules is preferably in a range of about 0.3 to 3 mm in terms of productivity.

The tablet may have any shape. Examples include a round shape, an oval shape, a spherical shape, a rod-like shape, a toroidal shape, a multilayer tablet, and a dry-coated tablet.

Examples of tablets include uncoated tablets (bare tablets), in particular, orally disintegrating tablets (OD tablets). The printing on the tablet surface can be performed also on tablets with small surface strength such as uncoated tablets (bare tablets), in particular, orally disintegrating tablets, by using the ink for inkjet printers mentioned below; thus, the effect of the present invention can be sufficiently exhibited for such tablets. For example, commercially available tablets such as Pletal OD tablets (Otsuka Pharmaceutical Co., Ltd.), Abilify tablets (Otsuka Pharmaceutical Co., Ltd.), and the like may also be used. Examples of tablets further include tablets disclosed in JP2011-513194A, JP2012-501960A, and JP2003-40764A.

When the tablets are orally disintegrating tablets, the pharmacologically active substance incorporated in the tablet is preferably cilostazol, aripiprazole, or the like.

When the tablets are orally disintegrating tablets, the orally disintegrating tablets are preferably obtained, for example, by incorporating particles in which an inorganic substance and a disintegrant are uniformly dispersed in composite particles of two or more kinds of sugar to the pharmacologically active substance, and then incorporating a fluidizer and an organic excipient.

The above granulation particles, in which an inorganic substance and a disintegrant are uniformly dispersed in composite particles of two or more kinds of sugar ("granulation particles"), are obtained by dispersing mannitol, sugar other than mannitol, a disintegrant, and an inorganic substance in water, followed by spray drying. A specific example is a composition for an orally disintegrating tablet produced by using the method disclosed in the international publication WO 2005/037254 or the international publication WO 2005/037319. The two or more kinds of sugar incorporated in the granulation particles are a combination of mannitol and other sugar. The term "sugar" encompasses sugar and sugar alcohol. Examples of the sugar other than mannitol include sugars and sugar alcohols listed above as examples of the excipient. A combination of mannitol and xylitol is preferable.

The weight ratio of mannitol to sugar other than mannitol is generally about mannitol:non-mannitol sugar=98:2 to 67:33, preferably about mannitol:non-mannitol sugar=97:3 to 87:13, further preferably about mannitol:non-mannitol sugar=96:4 to 89:11.

For the inorganic substance incorporated in the granulation particles, the substances listed above as examples of the excipient may be used. Preferably, the inorganic substance is at least one member selected from the group consisting of magnesium aluminometasilicate, magnesium aluminosilicate, calcium hydrogen-phosphate, anhydrous calcium hydrogen-phosphate, anhydrous calcium hydrogen-phosphate agglomerated substances, hydrotalcite, calcium carbonate, calcium silicate, and aluminum hydroxide dried gel. More preferably, the inorganic substance is at least one member selected from the group consisting of magnesium aluminometasilicate, hydrotalcite, anhydrous calcium hydrogen-phosphate and calcium carbonate. The average particle diameter of the inorganic substance is generally about 0.1 to 100 μm, preferably about 1 to 60 μm, further preferably about 1 to 40 μm.

To obtain the desired average particle diameter, an inorganic substance obtained through standard pulverization may be used.

For the disintegrant to be incorporated in the granulation particles, the disintegrants listed above may be used.

Crospovidon and crystalline cellulose are more preferable. When Crospovidon and crystalline cellulose are used, the weight ratio of Crospovidon to crystalline cellulose is generally about 5:8 to 15:22, preferably about 5:10 to 14:22, further preferably about 6:12 to 13:21. Generally, the average particle diameter of the disintegrant is preferably about 0.1 to 100 μm, more preferably about 1 to 60 μm, further preferably about 1 to 40 μm in terms of uniform dispersibility and prevention of rough texture in the oral cavity. To ensure the desired average particle diameter, the disintegrant obtained through standard pulverization may be used.

The amounts of the components of the granulation particles are as follows. The granulation particles contain about 40 to 90 parts by weight of sugar, about 1 to 30 parts by weight of inorganic substance, about 5 to 40 parts by weight of disintegrant, based on the total parts by weight, i.e., 100 parts by weight of the granulation particles. More preferably, granulation particles contain about 50 to 80 parts by weight of sugar, about 2 to 15 parts by weight of inorganic substance, and about 10 to 36 parts by weight of disintegrant, based on the total parts by weight, i.e., 100 parts by weight of the granulation particles. Further preferably, granulation particles contain about 62 to 78 parts by weight of sugar, about 3 to 8 parts by weight of inorganic substance, and about 18 to 34 parts by weight of disintegrant, based on the total parts by weight, i.e., 100 parts by weight of the granulation particles. The granulation particles may be produced by using a generally known wet granulation method, such as spray drying method, fluidized bed granulation drying method, stirring granulation method, or wet extrusion granulation method. The method disclosed in the international publication WO 2007/029376 may be used. These granulation particles are commercially available, for example, as F-MELT (registered trademark, Fuji Chemical Industry Co., Ltd.).

The content of the granulation particles in the tablet (orally disintegrating tablet) is generally about 10 to 60 wt %, preferably about 20 to 40 wt %.

When the tablets are orally disintegrating tablets, the incorporated fluidizer may be selected from the fluidizers listed above. Light anhydrous silicic acid is preferable. The content of the fluidizer in the tablet (orally disintegrating tablet) is generally about 0.2 to 2 wt %, preferably about 0.5 to 1.5 wt %.

When the tablets are orally disintegrating tablets, the celluloses and starches used as other excipients may be selected from those listed above. Among various celluloses, crystalline cellulose and carboxymethylcellulose are preferable. Crystalline cellulose is further preferable. Among various starches, corn starch, rice starch, potato starch, partly pregelatinized starch, and hydroxypropyl starch are preferable. Corn starch is further preferable. These components may be used soley or in a combination of two or more. A combination of crystalline cellulose and corn starch is preferable. The content of the organic excipient in the tablet (orally disintegrating tablet) is generally about 5 to 60 wt %, preferably about 10 to 30 wt %.

Further, the tablet may contain various additives generally used for the production of tablets insofar as the disintegration and moldability of the orally disintegrating tablets are not impaired. Examples of additives include lubricants, sweetening agents, taste-correcting agents, flavors, binders, and coloring agents. These additives may be selected from those listed above.

These additives are used solely or in a combination in the amounts desired. When the tablets are orally disintegrating tablets, the tablets are produced, for example, by using a method of weighing the pharmacologically active substance and other preparation materials, mixing them with an appropriate mixer such as a V-type mixer, and directly tabletting the resulting mixed powder for making tablets by compression.

The mixed powder for making tablets may be obtained by using an intensive mixing method using a stirring granulator, or a mixing pulverization method using a pulverizer. It is also possible to use a compression granulation method using a dry granulator, a wet granulation method using water, acetone, ethyl alcohol, propyl alcohol or a mixture of these, in which a binder is dispersed or dissolved as necessary, or a method of producing two or more different powders separately, and producing mixture powder for making tablets. When the mixture powder for making tablets is produced, lubricants, sweetening agents, taste-correcting agents, flavors, binders, coloring agents and the like may be added.

Preferably, first, a pharmacologically active substance and a fluidizer are sufficiently mixed, and then an organic excipient, granulation particles, a sweetening agent and a lubricant are added thereto, followed by sufficient mixing.

The resulting mixture powder for making tablets are subjected to compression molding, using, for example, a single-punch tablet machine or a rotary tablet machine, by applying a pressure of about 200 to 600 kg/pestle. Applying a pressure below or above this range is not preferable, because when the pressure is below this range, the hardness of the tablets becomes insufficient, and sufficient tablet hardness in handling cannot be ensured. Pressure above this range is also not preferable, because it causes delay in disintegration.

The compression molding may be performed by using a general tabletting method or an external lubrication tabletting method. By using an external lubrication tabletting method, it is possible to reduce the amount of the lubricant added, increase the integration rate, and increase the tablet hardness.

When the tablets are orally disintegrating tablets, the tablets will be rapidly disintegrated by saliva in the oral cavity, and thus smoothly ingested. Typically, the tablet hardness (measurement value obtained with a tablet hardness meter) is 30N or more, and the disintegration time in the oral cavity of a healthy adult is generally 90 seconds or less, preferably 60 seconds or less, more preferably 40 seconds or less.

The dry-ink film printed on the surface of the tablet contains a resin and a pigment.

Examples of pigment include black color materials such as carbon powder pigment (bamboo charcoal, Bincho charcoal, vegetable black), squid ink pigment, or activated carbon; white color materials such as titanium oxide, or calcium carbonate; and food dyes (edible dyes) such as aluminum lake (red lake, yellow lake, blue lake).

In particular, by using a black color material as a pigment, good pigment concentration and reflection density of the dry-ink film, good identification of the dry-ink film, good hardness of the dry-ink film, and a good printing effect (prevention of bleeding) are ensured, and resolving the problem of the printed characters peeling off or the printed characters transferring onto another tablet by contact. For the pigment, it is preferable to use pigments approved by the Food Sanitation Act or the Pharmaceutical Affairs Act.

Among black color materials, carbon powder pigment is preferable as an edible and opaque color material.

The carbon powder pigment is not particularly limited insofar as it is approved as a food additive. However, preferable is a carbon powder pigment containing carbon obtained from plant carbonization as a major ingredient. Among such plant-derived carbon powder pigments, pigments obtained by roasting cacao shells are commonly known. In addition, for example, pigments obtained by carbonizing plants by heating at a high temperature according to steam activation methods or the like are also approved as a food additive pigment. Further, examples of plant-derived carbon powder pigments also include bamboo charcoal, which is a bamboo-derived carbide, and charcoal of broad-leaved plants or needle-leaved plants.

In the present invention, among various plant-derived carbon powder pigments, carbon powder pigments obtained from broad-leaved plants such as various oaks, including Kashi, Nara (Japanese oak), Shii (chinquapin), Kashiwa (Japanese emperor oak) and the like are preferable. In particular, it is preferable to use Bincho charcoal obtained from Ubamegashi (*Quercus phillyraeoides*) or the like. Bincho charcoal is produced in the Kishu and Tosa regions, and has a porous structure. The structure is presumably derived from the plant structure before being carbonized. With the porous structure, although Bincho charcoal is very hard, its micronization, which is required when printing with an inkjet printer, is relatively easy. Further, since Bincho charcoal has a large carbon content, good blackness is more easily obtained when it is processed into ink. Moreover, since Bincho charcoal has a long history as a food material, it is a valuable material that ensures safety in use for food. Further, Bincho charcoal has lower electric resistance than does bamboo charcoal and is not easily affected by static electricity during ink production, and is thus easily treatable.

Such carbon powder pigments, including Bincho charcoal, are generally available in the form of a block, and are therefore roughly pulverized with a pulverizer, and then micronized before use, to make them more easily dispersed. The micronization may be performed by using various versatile pulverizers for applying mechanical impact. Further micronization may be performed using a micronization pulverizer, such as a jet mill, a bead mill, or the like. Then, to obtain an inkjet ink, the micronized carbon powder pigment is dispersed in an edible resin.

The content of the pigment in the dry-ink film is generally about 1.2 to 6 wt %, preferably about 1.5 to 5 wt % based on the entire dry-ink film. By specifying the content of the pigment in the dry-ink film to 1.2 wt % or more, a sufficient printing density is ensured. Further, by specifying the content of the pigment in the dry-ink film to 6 wt % or less, it is possible to increase the content of the resin in the dry-ink film, thereby increasing the strength of the dry-ink film and thus preventing the detachment of the dry-ink film.

An edible resin is preferable as the resin to be incorporated in the dry-ink film in view of good dispersion of the pigment in the dry-ink film, good adherence of the dry-ink film to the tablet, and the good strength of the dry-ink film. Examples of the resin include shellac, cellulose-based resin (such as hydroxypropyl cellulose, hydroxypropylmethyl cellulose, carboxymethyl cellulose, or methylcellulose), crystalline cellulose, gelatin, casein, soy protein, gum arabic cyclo dextrin, dammar resin, and copal resin. It is possible to use cellulose-based resins with various molecular weights, but cellulose-based resins with low molecular weights are preferable in terms of the dispersibility of the pigment in the dry-ink film and the good properties of the dry-ink film. It is preferable to use a resin approved by the Food Sanitation Act or the Pharmaceutical Affairs Act.

The content of the resin in the dry-ink film is preferably about 70 to 90 wt %, more preferably about 72 to 88 wt %, based on the entire dry-ink film. Specifying the content of the resin in the dry-ink film to 70 wt % or more provides a good effect of increasing the strength of the dry-ink film, thereby preventing the detachment of the dry-ink film. Further, by specifying the content of the resin in the dry-ink film to 90 wt % or less, it is possible to increase the amount of the pigment in the dry-ink film, thereby ensuring a sufficient printing density.

The resin preferably contains shellac. When the resin contains shellac, the content of the shellac in the total resin is preferably 90 wt % or more, more preferably 92 wt % or more, further preferably 95 wt % or more.

Further, as a combination of multiple resins, a combination of shellac and a cellulose-based resin is preferable. A combination of shellac and hydroxypropyl cellulose or a combination of shellac and hydroxypropylmethyl cellulose is more preferable because they enable dispersion of the pigment, in particular, carbon powder pigment.

When the resin is a combination of shellac and a cellulose-based resin, the content ratio of cellulose-based resin to shellac is generally about 0.001 to 0.1 parts by weight, and preferably about 0.002 to 0.05 parts by weight, per part by weight of shellac.

Further, the dammar resin or copal resin mentioned above may be added as an additive to the combination of shellac and cellulose-based resin.

Shellac is an edible resin obtained by purifying a resin-like substance derived from lac insects, and is available as a mixture of various kinds of resin acid and esters thereof, wax, and pigment. Alcohol-soluble shellac is particularly preferable. Further, white shellac, which is purified shellac, is preferable in terms of quality stability. Shellac is conducive to dispersion of the pigment and the fixation of the pigment by friction resistance.

Further, the content ratio of the pigment (P) to the resin (B) (P/B ratio) is important to ensure the hardness matching the material of the tablet surface. With this hardness, it is possible to immediately obtain the hardness of the dry-ink film against contact between the tablets in the step of conveying the tablets or the friction in the portions of the tablets in contact with the conveyer immediately after printing.

The content of the resin to the pigment is 15 to 50 parts by weight, preferably about 17 to 50 parts by weight, per weight of the pigment, in terms of superior adherence of the dry-ink film onto the surface of the tablet, superior hardness of the dry-ink film, prevention of the transfer of the dry-ink film onto another tablet or the conveyer in the conveying step when printing, or generation of smudges.

In addition to the pigment and resin mentioned above, the dry-ink film may contain, for example, sodium lactate, sodium acetate, sodium pantothenate, and the like.

The hardness of the dry-ink film is preferably 2B to 4H, and more preferably HB to 4H. Such hardness of the dry-ink film is preferable in terms of preventing transfer or detachment of the dry-ink film due to the friction between multiple dry-ink films, or between a dry-ink film and an unprinted portion of the tablet surface. The hardness of the dry-ink film of the tablet may be measured as pencil hardness according to JIS K 5600-5-4.

The reflection density of the dry-ink film (printed dot) on the tablet surface is preferably about 0.1 to 0.3 in terms of its legibility and preventing user reluctance (misunderstanding or misperception of the ink film as a smudge) regarding the tablet as a pharmaceutical tablet. The reflection density of the dry-ink film of the tablet can be measured by measuring the reflection density of the dots in the dry ink film by using a micro-surface color difference meter (a micro colormeter). A VSR400 available from Nippon Denshoku Kogyo KK may be used as the micro-surface color difference meter (a micro colormeter).

2. Ink for Inkjet Printers

The ink for inkjet printers of the present invention is characterized by containing a resin and a pigment at a specific content ratio. Further, the ink for inkjet printers of the present invention can be used to print on a tablet surface.

The ink for inkjet printing in the present invention is preferably used for printing on a tablet having a surface containing 0.2 wt % or less, preferably 0.1 wt % or less, more preferably 0.06 wt % or less, of powder based on the total weight of the tablet, in terms of preventing the problem of the dry-ink film becoming detached or the dry-ink film transferring onto another tablet by contact. Such a tablet as this, which has a surface containing a small amount of powder, is obtained by using the method described in "1. Tablet Having a Dry-ink Film" above, or a similar method.

The ink for inkjet printers of the present invention can be used for printing on a tablet having a surface hardness of generally 5 to 300 g, preferably 5 to 100 g, more preferably 5 to 50 g, further preferably 5 to 20 g. In particular, the ink for inkjet printers of the present invention can be used for printing on a tablet with a soft surface having a hardness of 5 to 100 g (more preferably 5 to 50 g, further preferably 5 to 20 g). Examples of such a tablet include the tablets disclosed in "1. Tablet Having a Dry-ink Film" above.

Examples of pigment include the pigments disclosed in "1. Tablet Having a Dry-ink film" above. In particular, in black printing, using the above black color materials ensures good pigment concentration and reflection density of the dry-ink film, good identification of the dry-ink film, good hardness of the dry-ink film, and good printing effect (prevention of bleeding), thereby resolving the problem of the printed characters peeling off or the printed characters transferring onto another tablet by contact.

Among black color materials, carbon powder pigment is more preferable as a food dye (an edible dye) and as an opaque color material.

Examples of carbon powder pigments to be used as the pigment may be selected from those disclosed as the pigments contained in the dry-ink film in "1. Tablet Having a Dry-ink Film" above. In particular, it is preferable to use Bincho charcoal obtained from Ubamegashi (*Quercus phillyraeoides*) or the like. Bincho charcoal has lower electric resistance than does bamboo charcoal and is not easily affected by static electricity during ink production. The carbon powder pigments, including Bincho charcoal, are generally available in the form of a block and are thus roughly pulverized with a pulverizer and then micronized before use to make them more easily dispersed. The micronization may be performed by using various versatile pulverizers for applying mechanical impact. Further micronization may be performed using a micronization pulverizer, such as a jet mill. Then, to obtain an inkjet ink, the micronized carbon powder pigment is dispersed in an edible resin.

The pigment to be used as a material of the ink for inkjet printers preferably has an average particle diameter of about 0.01 to 10 µm, more preferably about 0.05 to 3 µm, further preferably about 0.05 to 1 µm. Specifying the average particle diameter to 10 µm or less is preferable since it becomes possible to perform sufficient dispersion in the resin in a relatively short time, and since excessive influence by heat can be prevented and the characteristics of the resin can be maintained. Further, by specifying the average particle diameter of the pigment to 3 µm or less, it becomes possible to avoid the occurrence of pigment sedimentation during the storage of the ink for inkjet printers, thus preventing the piping system of the printer from becoming blocked with the ink. Further, specifying the average particle diameter of the pigment to 0.01 µm or more is preferable since it becomes possible to reduce a decrease in printing density. Further, by specifying the average particle diameter of the pigment to 0.05 µm or more, a large dispersion energy is not required, and thus is preferable in terms of costs and in terms of preventing transparency. The ink obtained by incorporating a pigment having such a range of average particle diameter ensures good opacity and color reproduction of the pigment. The average particle diameter of the carbon powder pigment dispersed when the ink is prepared may be measured using laser light with various particle size distribution meters, such as a light-scattering particle size distribution meter.

The adjustment of the average particle diameter of the pigment as described above may be performed by using a horizontal sand mill.

To disperse the pigment in the resin, it is possible to suitably select a method of rolling the pigment and the resin between two rolls into a plate, a method of rolling a highly viscous mixture of the pigment and the resin with three rolls, a method of dispersing intermediate-viscous mixture with a high-speed agitator mill, or a method of reducing the solvent content and applying an impact on the pigment and the resin with a ball mill. However, considering the mixing state with the resin solution at dispersion, dispersion is preferably performed using a horizontal sand mill with zirconia beads or the like as dispersion media.

Although the content of the pigment in the ink for inkjet printers depends on the content of other components in the present invention, it is preferably about 0.05 to 0.7 wt %, more preferably about 0.1 to 0.6 wt %. By specifying the content of the pigment to 0.05 wt % or more, the printing can be performed with sufficient printing density. Further, by specifying the content of the pigment to 0.7 wt % or less, it is possible to decrease the relative content of resin in the ink, thereby preventing excessive increase in viscosity. Therefore, it is possible to reduce the decrease in continuous printability in an ink-jet printer. In particular, it is also preferable in terms of stability in continuing recording (reducing curved ejection or scattering of the ink droplets).

The resin is incorporated in the ink for inkjet printers in order to satisfactorily disperse the pigment and ensure the adherence of the ink to the tablet as well as the strength of the dry-ink film printed on the tablet. The resin is preferably an edible resin. Examples include the resins contained in the dry-ink film described in "1. Tablet Having a Dry-ink Film".

Among these resins, incorporation of shellac provides dispersibility of the pigment (in particular, carbon powder pigment) and ensures superior fixation, thereby ensuring friction resistance. Further, by being dissolved in a solvent such as alcohol, shellac also serves to increase the viscosity of the ink. Also, shellac can be dissolved in a mixed solvent containing water and alcohol.

When shellac is incorporated in the resin, the content of the shellac in the entire resin is preferably 90 wt % or more, more preferably 92 wt % or more, further preferably 95 wt % or more.

Shellac thus serves as a preferable binder also in terms of its usability in a solvent containing water. Further, a combination of shellac and a cellulose-based resin is more preferable. A combination of shellac and hydroxypropyl cellulose, or a combination of shellac and hydroxypropyl methyl cellulose is further preferable because it enables dispersion of the pigment (in particular, carbon powder pigment). When a combination of shellac and a cellulose-based resin is used as the resin, the content ratio of the cellulose-based resin is preferably about 0.001 to 0.1 parts by weight, more preferably about 0.002 to 0.05 parts by weight, per part by weight of shellac.

The cellulose-based resin is used by being dissolved in water, or in a mixed solution of water and alcohol.

Further, when a combination of shellac and cellulose-based resin is used as the resin, the pigment is first dispersed in an aqueous solution of a cellulose-based resin before the dispersion of the pigment and the shellac, and then the mixture is dispersed in a shellac solution. In this manner, good dispersion stability can be maintained. To maintain the dispersion stability well, a cellulose-based resin soluble in water and alcohol is suitable. In particular, it is preferable to use hydroxypropyl cellulose highly soluble both in water and alcohol.

It is possible to use cellulose-based resins with various molecular weights, but cellulose-based resins with low molecular weights are preferable in terms of the above dispersibility and the appropriate viscosity. In particular, it is more preferable to use a resin that has a molecular weight for providing a viscosity of about 1 to 7 mPa·s in an aqueous solution that has a 2 wt % concentration at 20° C.

The content of the resin in the ink is preferably about 0.75 to 25 wt %, more preferably about 2 to 15 wt %. Specifying the content of the resin to 0.75 wt % or more is preferable because it provides the ink with an appropriate viscosity. Further, the above content is preferable also in terms of sufficient adherence onto the tablets. Further, by specifying the content of the resin to 25 wt % or less, the viscosity of the ink does not excessively increase, and the fluidity does not decrease even at a low temperature, thereby preventing a decrease in stability upon printing by an inkjet printer.

Further, the content ratio of the pigment (pigment) to the resin (binder) (P/B ratio) is important for the ink for inkjet printers of the present invention in terms of avoiding the transfer or the detachment of the dry-ink film due to contact between the tablets or due to friction or the like at the contact portions of the tablet with the conveyer in the step of conveying the tablets immediately after the printing.

Specifically, the content of the resin per part by weight of the pigment is about 15 to 50 parts by weight, preferably about 17 to 50 parts by weight. By specifying the content of the resin to 15 parts by weight or more, superior dispersibility of the pigment is obtained, thereby ensuring superior adherence of the ink onto the tablet surface, and superior hardness of the dry-ink film after printing. Further, specifying the content of the resin to 50 parts by weight or less is preferable in terms of ensuring sufficient solubility of the resin itself and avoiding an increase in viscosity after dispersion.

When the resin is partially mixed with water, it is preferable to adjust the pH of the ink to be alkaline, i.e., about 7.5 to 10.5, so as to maintain stable solubility. By specifying the pH of the ink to 7.5 or more, it is possible to prevent precipitation of the resin, in particular, the shellac. Further, by specifying the pH of the ink to 10.5 or less, it is possible to prevent the odor derived from the pH adjuster in the printer or when printing is performed.

The pH adjuster for adjusting the pH of the ink within the above range is preferably a food additive that volatilizes after the printing in terms of the water resistance. Examples of pH adjusters include ammonium carbonate, ammonium hydrogencarbonate, ammonia, and ammonium chloride. Among these, it is preferable to adjust the pH by using ammonium hydroxide or ammonium carbonate in terms of the problem of residues.

The ink for inkjet printers of the present invention may be used for a continuous inkjet printer. When the ink is used for a continuous inkjet printer, the electroconductivity of the ink is adjusted according to the printer. The electroconductivity is adjusted by using a conducting agent.

Examples of conducting agent include agents approved as food additives, such as sodium lactate, sodium acetate, sodium pantothenate and the like. Among these, since sodium lactate is dissolved well in a solvent containing alcohol, it enables the electroconductivity of the ink droplet in the printer to be appropriately maintained even with a small amount.

Although content of the conducting agent in the entire ink depends on the content, i.e., the parts by weight, of other components, it is preferably about 0.1 to 2.0 wt %. By using such an amount of a conducting agent, it is possible to ensure appropriate electroconductivity of the ink, namely about 0.5 to 5 mS/cm. Although the above range is allowable, it is preferable to use a small amount of a conducting agent in the adjustment of electroconductivity. By specifying the content of the conducting agent to 2.0 wt % or less, it is possible to avoid the aggregation of the pigment.

The ink for inkjet printers of the present invention preferably contains one or more solvents. The content of the solvent in the entire ink is about 50 to 98 wt %. In particular, it is preferable to use alcohol in terms of its superior drying and its affinity for the tablet surface to be printed on. It is more preferable to use ethanol as a major ingredient of the solvent.

The content of the alcohol in the ink is preferably 50 wt % or more. This content is preferable in terms of superior drying of the tablet surface and superior friction resistance of the dry-ink film formed of the resulting ink. Further, depending on the printing system, it is possible to perform high-speed printing of variable information. The ethanol that can be used in the present invention is denatured ethanol or fermentation ethanol for food.

Further, it is preferable to further incorporate water as the solvent. The content of water is preferably about 3 to 21 wt % based on the entire ink. By specifying the content of water to 3 wt % or more, the dispersion stability of the pigment is ensured. Further, specifying the content of water to 21 wt % or less is preferable in terms of ensuring quick drying when alcohol is used as a solvent.

Further, it is preferable that the ink for inkjet printers of the present invention contain a resin and a pigment, that the ink contain 15 to 50 parts by weight of resin per part of the pigment, that the resin contain shellac, and that the pigment contain a carbon powder pigment. Such an ink is preferable in terms of adjusting the hardness of the dry-ink film, which is formed by drying the ink, to a pencil hardness of 2B to 4H, and adjusting the reflection density of the dry-ink film to 0.1 to 0.3. This ink has superior printability and has adequate viscosity for the printing using a continuous inkjet printer, thereby ensuring stable discharge. Further, since the dry-ink film formed after the printing has a specific pencil hardness and specific reflection density, the printed characters are good in terms of legibility, transfer, and detachment.

The ink of the present invention thus has superior characteristics and therefore enables printing on various tablets ranging from tablets with a hard surface such as film-coated tablets to tablets with a soft surface such as uncoated tablet (e.g., bare tablets and OD tablets). In particular, the ink is suitable for printing on a tablet with a soft surface such as an uncoated tablet. For printing on uncoated tablets, better printing can be performed by specifying the amount of the powder in the tablet surface to 0.2 wt % or less.

Further, since the ink of the present invention is edible, it enables printing on foods with hard or soft surfaces, as well as on tablets.

The method for producing the ink for inkjet printers of the present invention is not particularly limited. The ink for inkjet printers of the present invention may be produced by using a known method. For example, when shellac and a cellulose-based resin are used as resin components, the ink is produced through the following steps.

Step 1: a step of mixing a cellulose-based resin and water or a mixture solution of water and alcohol to prepare a cellulose-based resin solution, and then adding a pigment thereto to obtain a pigment dispersion.

Step 2: a step of mixing shellac and alcohol, thereby preparing a shellac-containing alcohol solution.

Step 3: a step of mixing the dispersion obtained in Step 1 with the shellac-containing alcohol solution obtained in Step 2, thereby preparing an ink for inkjet printers.

Resins other than shellac or cellulose-based resin, a pH adjuster, and a conducting agent may be added in any of Steps 1 to 3; however, they are preferably added in Step 3.

The amounts and the proportions of the components used in Steps 1 to 3 are suitably adjusted according to the specified amounts and proportions of the components of the ink for inkjet printers detailed above.

The liquid for dissolving the cellulose-based resin in Step 1 is preferably water, or a solvent containing 50 wt % or more of water and less than 50 wt % of ethanol. Specifying the ethanol content to less than 50 wt % in the solvent is preferable in terms of ensuring stable dispersibility of the pigment in the solvent. In particular, with this content it is possible to prevent the decrease in dispersion stability during the dispersion in the shellac solution in Step 2, and also avoid aggregation during the addition of the conducting agent.

3. Method for Producing Tablet Having a Dry-ink Film

The method for producing the tablet described in "1. Tablet Having a Dry-ink Film" above includes a step of printing characters on a surface of a tablet with a specific surface hardness by using an ink for inkjet printers.

Examples of the tablet include the tablets described in "1. Tablet Having a Dry-ink Film" above. By using an ink for inkjet printers, it is possible to perform printing also on a tablet having a small surface strength, such as an uncoated tablet (bare tablet), in particular, an orally disintegrating tablet.

The printing is preferably performed on a tablet containing 0.2 wt % or less, preferably 0.1 wt % or less, more preferably 0.06 wt % or less, of powder on the surface based on the total weight of the tablet, because such printing does not suffer from the problems of the dry-ink film becoming detached or the dry-ink film transferring onto another tablet by contact. A tablet containing a small amount of powder in the tablet surface, such as described above, is obtained by using the method described above or a similar method.

The tablet to be printed on by using the ink of the present invention is not particularly limited. Examples include various tablets from film-coated tablets with a hard surface to uncoated tablets with a soft surface. Further, the ink of the present invention is preferably used for the printing of tablets with a soft surface, such as uncoated tablets. Accordingly, surface hardness of the tablet is generally about 5 to 300 g, preferably about 5 to 100 g, more preferably about 5 to 50 g, further preferably about 5 to 20 g. The surface hardness of the tablet is measured by using the method described above, or a similar method.

For the ink for inkjet printers, the ink described in "2. Ink for Inkjet Printers" above may be used.

The content of the resin per part by weight of the pigment is 15 to 50 parts by weight, preferably about 17 to 50 parts by weight. By specifying the content of the resin to 15 parts by weight or more, it is possible to ensure superior dispersibility of the pigment, thereby ensuring superior adherence of the ink onto the tablet surface and superior hardness of the dry-ink film obtained after the printing. Further, specifying the content of the resin to 50 parts by weight or less is preferable in terms of ensuring sufficient solubility of the resin itself, and preventing an increase in viscosity when dispersion is performed.

The printing on a tablet surface by using the ink for inkjet printers is preferably performed using an inkjet printer. Specifically, it is preferable to perform printing using a continuous inkjet printer (charge control system). For example, it is possible to use an inkjet printer disclosed in JP 2008-137197A, JP 2005-035210A, or the like.

EXAMPLES

The present invention is explained below in further detail with reference to Examples, etc. However, the scope of the invention is not limited to these Examples.

Examples 1 to 7 and Comparative Examples 1 to 3 (Preparation of Ink for Inkjet Printers)

To prepare ink for inkjet printers, the following dispersion and shellac solution were prepared, and then, ink for inkjet printers was prepared using the dispersion and the shellac solution.

Preparation of Dispersion

Three parts by weight of hydroxypropyl cellulose (HPC) (viscosity: 2.5 mPa·s (2 wt % aqueous solution, 20° C.)) or hydroxypropyl methylcellulose (HPMC) (viscosity: 4.0 mPa·s (2 wt % aqueous solution, 20° C.)) was dissolved in 97 parts by weight of water, thereby preparing a HPC solution or a HPMC solution having a concentration of 3 wt %.

The HPC solution or HPMC solution having a concentration of 3 wt % prepared above was mixed with Ubamegashi (*Quercus phillyraeoides*)-derived Bincho charcoal according to the compounding proportions shown in the "Dispersion (containing 10 wt % of carbon powder pigments)" column in Table 1, thereby preparing a mill base. Thereafter, the resulting mill base was dispersed for 2 hours using a horizontal mill containing zirconia beads, thereby preparing a dispersion in which Bincho charcoal (carbon powder pigments) with an average particle diameter of 0.31 μm is dispersed.

Preparation of Shellac Solution

White shellac was added to ethanol (99%) according to the compounding proportions shown in the "25 wt % shellac solution" column in Table 1, and the resulting mixture was stirred, thereby preparing a shellac-containing ethanol solution having a concentration of 25 wt % (25 wt % shellac solution).

Preparation of Ink for Inkjet Printers

The 25 wt % shellac solution prepared above, ammonium carbonate, 50 wt % sodium lactate aqueous solution, ethanol, and purified water were added to the dispersion prepared above according to the compounding proportions shown in Table 1, and the mixture was well stirred, thereby preparing a dispersion of ink. The resulting dispersion was filtrated with a No. 63 filter. The resulting liquid was filtrated using a filter with 0.8-μm openings, thereby preparing ink for inkjet printers.

Table 1 shows the dispersion, the shellac solution, and other components of the ink for inkjet printers of Examples 1 to 7 and Comparative Examples 1 to 3, as well as their compounding proportions. Further, Table 2 shows the components of the inks for inkjet printers of Examples 1 to 7, and Comparative Examples 1 to 3, and their compounding proportions.

TABLE 1

| Components (parts by weight) | Example 1 | Example 2 | Example 3 | Example 4 | Example 5 | Example 6 | Example 7 | Comparative Example 1 | Comparative Example 2 | Comparative Example 3 |
|---|---|---|---|---|---|---|---|---|---|---|
| Dispersion (containing 10 wt % carbon powder pigment) | | | | | | | | | | |
| carbon powder pigment | 0.3 | 0.5 | 0.4 | 0.25 | 0.4 | 0.3 | 0.7 | 2 | 3 | 1.5 |
| Hydroxy propylcellulose | 0.081 | 0.135 | 0.108 | — | 0.108 | 0.081 | 0.189 | 0.54 | 0.81 | 0.405 |
| Hydroxy propylmethylcellulose | — | — | — | 0.0675 | — | — | — | — | — | — |
| Water | 2.619 | 4.365 | 3.492 | 2.1825 | 3.492 | 2.619 | 6.111 | 17.46 | 26.19 | 13.095 |
| Total amount of dispersion | 3 | 5 | 4 | 2.5 | 4 | 3 | 7 | 20 | 30 | 15 |
| 25 wt % shellac solution | | | | | | | | | | |
| Shellac | 10 | 10 | 9 | 12.25 | 10 | 11 | 10.5 | 7 | 6.25 | 7.5 |
| Ethanol | 30 | 30 | 27 | 36.75 | 30 | 33 | 31.5 | 21 | 18.75 | 22.5 |
| Total amount of 25 wt % shellac solution | 40 | 40 | 36 | 49 | 40 | 44 | 42 | 28 | 25 | 30 |
| Ammonium carbonate | 1.5 | 1.5 | 2.3 | 2 | 1.5 | 1.5 | 1.5 | 1 | 1 | 1.5 |
| Ethanol | 37.2 | 43.8 | 40.7 | 35.5 | 37 | 36 | 37.5 | 49 | 42 | 47 |
| 50 wt % sodium lactate aqueous solution | | | | | | | | | | |
| Sodium lactate | 0.5 | — | — | 0.25 | — | — | — | 1 | 1 | 1 |
| Purified water | 0.5 | — | — | 0.25 | — | — | — | 1 | 1 | 1 |
| Total amount of 50 wt % sodium lactate aqueous solution | 1 | — | — | 0.5 | — | — | — | 2 | 2 | 2 |
| Purified water | 17.3 | 9.7 | 17 | 10.5 | 17.5 | 15.5 | 12 | | | 4.5 |

TABLE 2

| Components (parts by weight) | Example 1 | Example 2 | Example 3 | Example 4 | Example 5 | Example 6 | Example 7 | Comparative Example 1 | Comparative Example 2 | Comparative Example 3 |
|---|---|---|---|---|---|---|---|---|---|---|
| carbon powder pigment | 0.3 | 0.5 | 0.4 | 0.25 | 0.4 | 0.3 | 0.7 | 2 | 3 | 1.5 |
| Hydroxypropyl cellulose | 0.081 | 0.135 | 0.108 | — | 0.108 | 0.081 | 0.189 | — | 0.81 | 0.405 |
| Hydroxy propylmethylcellulose | — | — | — | 0.0675 | — | — | — | 0.54 | — | — |
| Shellac | 10 | 10 | 9 | 12.25 | 10 | 11 | 10.5 | 7 | 6.25 | 7.5 |
| Ethanol | 67.2 | 73.8 | 67.7 | 72.25 | 67 | 69 | 69 | 70 | 60.75 | 69.5 |
| Purified water | 20.419 | 14.065 | 20.492 | 12.9325 | 20.992 | 18.119 | 18.111 | 18.46 | 27.19 | 18.595 |
| Ammonium carbonate | 1.5 | 1.5 | 2.3 | 2 | 1.5 | 1.5 | 1.5 | 1 | 1 | 1.5 |
| Sodium lactate | 0.5 | — | — | 0.25 | — | — | — | 1 | 1 | 1 |
| Shellac/carbon powder pigment (weight ratio) | 33.33 | 20 | 22.5 | 49 | 25 | 36.67 | 15 | 3.5 | 2.08 | 5 |
| Resin (shellac + cellulose-based resin)/carbon powder pigment (weight ratio) | 33.6 | 20.27 | 22.77 | 49.27 | 25.27 | 36.94 | 15.27 | 3.77 | 2.35 | 5.27 |

Examples 8 to 14 and Comparative Examples 4 to 7 (Preparation of Tablet Printed with the Ink for Inkjet Printers)

Printing was performed on the commercially available tablets shown in Table 3 by using each ink for inkjet printers containing the components at the compounding proportions shown in Tables 1 and 2 by using an inkjet printer (40µ-nozzle CCS3000: Kishu Giken Kogyo Co., Ltd.). The tablets used were prepared by mildly vibrating the commercially available tablets shown in Table 3 on a 30-cm sieve while removing powder with a vacuum cleaner. In Examples 11 to 14 and Comparative Example 7, after the powder was removed, powder (crystalline cellulose: product name: Ceolus PH301 (Asahi Kasei Co., Ltd.)) was added to the surfaces of the tablets in a plastic bag so that powder in the specified amount in Table 4 was sufficiently adhered to each tablet before the printing.

TABLE 3

| Tablets | Hardness of Tablet Surface |
|---|---|
| Pletal OD tablet 100 mg (Tablet 1) | 6 g |
| Pletal OD tablet 100 mg (Tablet 2) | 16 g |
| Pletal OD tablet 50 mg (Tablet 3) | 16 g |
| Abilify tablet 6 mg (Tablet 4) | 19 g |
| Mucosta tablet (coated tablet) (Tablet 5) | 88 g |

Figure 4:
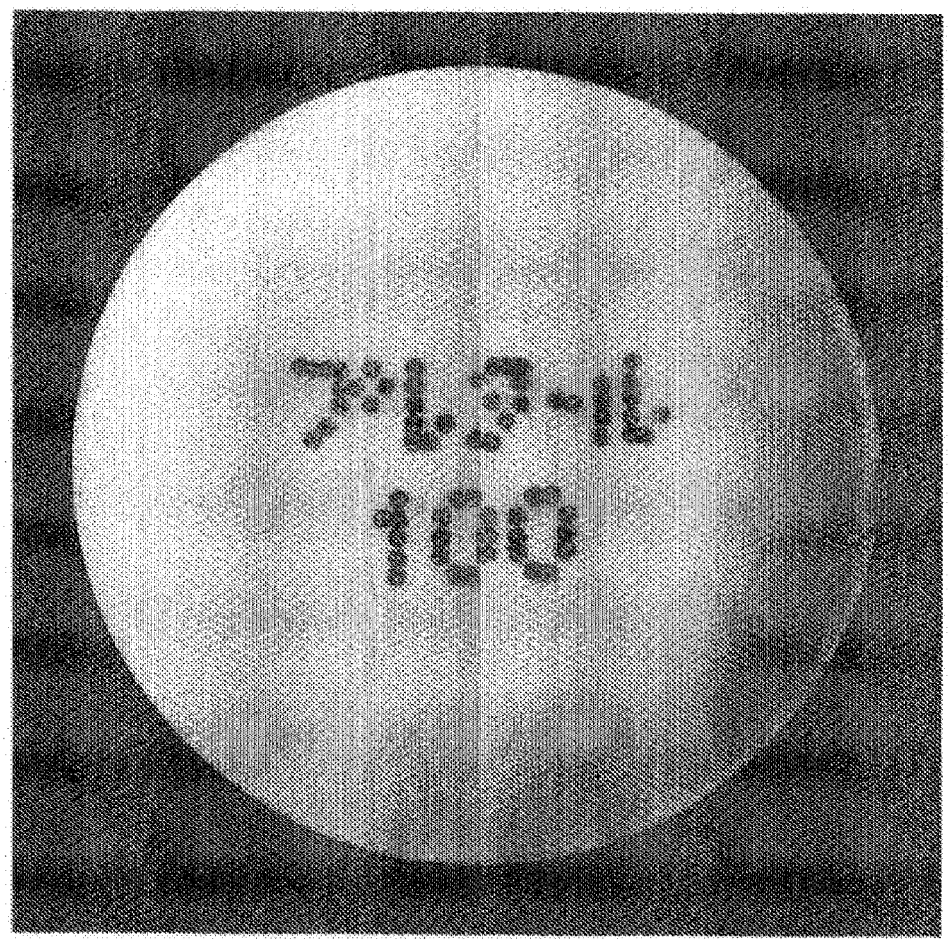
FIG. 4 shows a photo of a tablet of Example 10 that has a surface printed by using an inkjet method.
Figure 5:
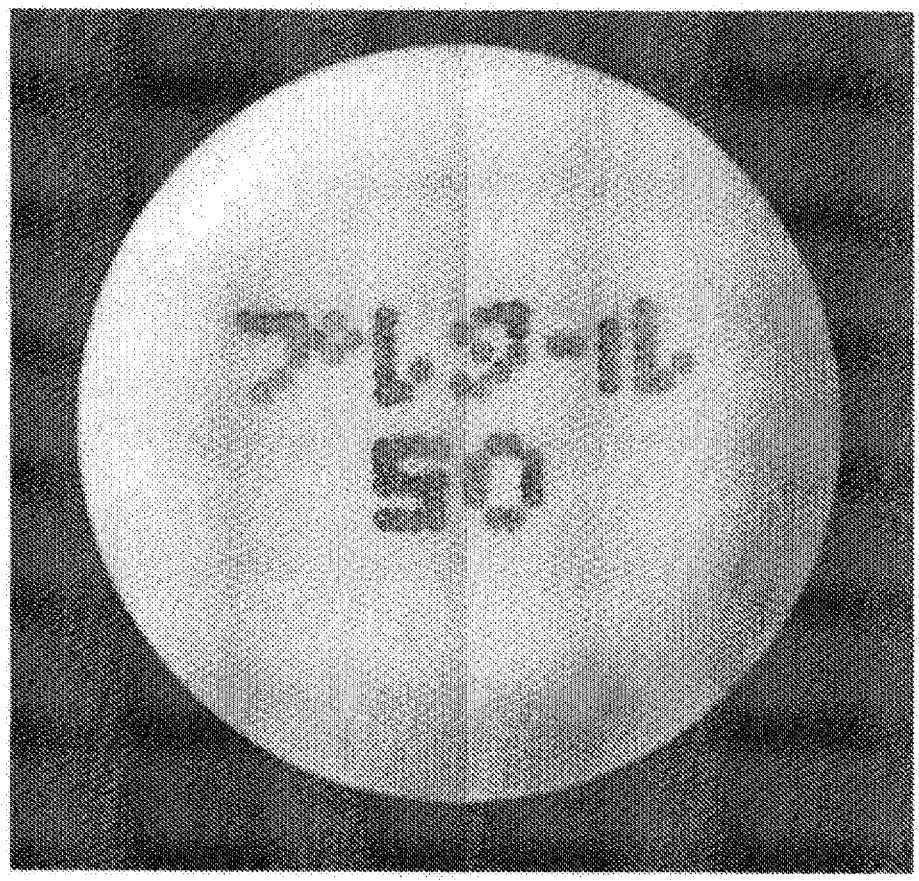
FIG. 5 shows a photo of a tablet of Example 12 that has a surface on printed by using an inkjet method.

The following properties were measured with respect to the resulting printed tablets. The measurements were performed using the methods below. Table 4 shows the evaluation results. Further, FIG. 4 shows a photo of a tablet of Example 10 having a surface printed by using an inkjet method, and FIG. 5 shows a photo of a tablet of Example 12 having a surface printed by using an inkjet method.

Hardness of Dry-ink Film

Smudge Due to Transfer of Printed Tablet Characters onto Another Tablet

The printed tablets were brought into contact with each other, and the degrees of smudging were tested using a printing inspection device, and evaluated using the percentage defective.

The samples with a percentage defective of 0.1% or less were ranked "o", and the samples with a percentage defective of more than 0.1% were ranked "x".

TABLE 4

| Evaluation of properties | Example 8 | Example 9 | Example 10 | Example 11 | Example 12 | Example 13 | Example 14 | Comparative Example 4 | Comparative Example 5 | Comparative Example 6 | Comparative Example 7 |
|---|---|---|---|---|---|---|---|---|---|---|---|
| Ink | Example 6 | Example 6 | Example 6 | Example 6 | Example 6 | Example 6 | Example 6 | Comparative Example 1 | Comparative Example 1 | Comparative Example 1 | Example 6 |
| Hardness of dry-ink film | HB | HB | HB | HB | HB | HB | HB | 6B | 6B | 6B | HB |
| Tablets | Tablet 5 | Tablet 4 | Tablet 1 | Tablet 4 | Tablet 3 | Tablet 4 | Tablet 5 | Tablet 5 | Tablet 4 | Tablet 1 | Tablet 4 |
| Hardness of tablet surface (g) | 88 | 19 | 6 | 19 | 16 | 19 | 88 | 88 | 19 | 6 | 19 |
| Proportion of powder in tablet surface (wt %) | 0.05 or less | 0.05 or less | 0.05 or less | 0.1 | 0.2 | 0.2 | 0.2 | 0.05 or less | 0.05 or less | 0.05 or less | 0.3 |
| Reflection density of dots in dry-ink film | 0.14 | 0.14 | 0.14 | 0.14 | 0.14 | 0.14 | 0.14 | 0.51 | 0.51 | 0.51 | 0.14 |
| Legibility | o | o | o | o | o | o | o | o | x | x | x |
| Detachment of printed dots | o | o | o | o | o | o | o | o | x | x | x |
| Smudge due to transfer of printed characters on tablet onto another tablet | o | o | o | o | o | o | o | x | x | x | o |

The hardness of the dry-ink film was measured as pencil hardness according to JIS K 5600-5-4. The hardness of the dry-ink film was measured by measuring the hardness of printed characters on a film which were printed with each ink for inkjet printers containing the components at the compounding proportions shown in Tables 1 and 2 by using an inkjet printer (40-μ nozzle CCS3000: Kishu Giken Kogyo Co., Ltd.).

Hardness of Tablet Surface

The critical load value at which the tablet surface is detached was measured according to the JIS R 3255 scratch test. The measurement was performed using a continuous loading surface measurement device (type: 22; Shinto Scientific Co., Ltd.) with a sapphire indenter with a radius of 0.1 mm at a movement rate of 0.1 mm/s.

Proportion of Powder in Tablet Surface

The weights of the tablet before and after removing the powder from the tablet surface were measured, and the proportion of the powder in the tablet surface was calculated from the difference.

Reflection Density of Dots in Dry-Ink Film

The reflection density of the dots in the dry-ink film on the tablet surface was measured using a micro-surface color difference meter (a micro colormeter) (VSR400: Nippon Denshoku Kogyo KK).

Legibility and Detachment of Printed Dots

Three seconds after the printing on the tablets, legibility and detachment of printed dots were tested using a printing inspection device, and evaluated using the percentage defective.

The samples with a percentage defective of 0.1% or less were ranked "o", and "the samples with a percentage defective of more than 0.1% were ranked "x".

Examples 15 to 21 and Comparative Examples 8 to 10 (Preparation of Tablet Printed with Ink for Inkjet Printers)

Printing was performed on the commercially available tablets mentioned above (100-mg Pletal OD tablets (surface hardness: 16 g)) using each ink for inkjet printers containing the components at the compounding proportions shown in Tables 1 and 2 by using an inkjet printer (40-μ nozzle CCS3000: Kishu Giken Kogyo Co., Ltd.). The content of the powder in the tablet surface was measured by using the same method as in Example 8, with the result that the content of the powder was 0.05 wt % or less.

The following properties were measured with respect to the resulting printed tablets. The measurements were performed using the methods below. Table 5 shows the evaluation results.

Hardness of Dry-Ink Film

The hardness of the dry-ink film was measured by using the same method as in Example 8.

Reflection Density of Dots of Dry-Ink Film

The reflection density of the dots of the dry-ink film was measured by using the same method as in Example 8.

Legibility and Detachment of Printed Dots

The legibility and detachment of the printed dots were measured by using the same method as in Example 8.

Smudge Due to Transfer of Printed Characters on Tablet onto Another Tablet

The smudges due to the transfer of the printed tablet characters onto another tablet were measured by using the same method as in Example 8 or a similar method.

TABLE 5

| Evaluation of properties | Example 15 | Example 16 | Example 17 | Example 18 | Example 19 | Example 20 | Example 21 | Comparative Example 8 | Comparative Example 9 | Comparative Example 10 |
|---|---|---|---|---|---|---|---|---|---|---|
| Ink | Example 1 | Example 2 | Example 3 | Example 4 | Example 5 | Example 6 | Example 7 | Comparative Example 1 | Comparative Example 2 | Comparative Example 3 |
| Hardness of dry-ink film | HB | HB | HB | HB | HB | HB | 2B | 6B | 6B | 6B |
| Proportion of powder in tablet surface (wt %) | 0.05 or less | 0.05 or less | 0.05 or less | 0.05 or less | 0.05 or less | 0.05 or less | 0.05 or less | 0.05 or less | 0.05 or less | 0.05 or less |
| Reflection density of dots in dry-ink film | 0.14 | 0.16 | 0.15 | 0.13 | 0.15 | 0.14 | 0.29 | 0.51 | 0.61 | 0.45 |
| Legibility | ○ | ○ | ○ | ○ | ○ | ○ | ○ | x | x | x |
| Detachment of printed dots | ○ | ○ | ○ | ○ | ○ | ○ | ○ | x | x | x |
| Smudge due to transfer of printed characters on tablet onto another tablet | ○ | ○ | ○ | ○ | ○ | ○ | ○ | x | x | x |

Results and Discussion

Each of the inks for inkjet printers of Examples 1 to 7 contains a large amount of shellac as a resin, namely, 15 to 49 parts by weight per part by weight of the carbon powder as a pigment, and thus contains a small amount of the pigment. Therefore, these inks had an adequate viscosity for the printing with a continuous inkjet printer. It was thus confirmed that these inks can be stably discharged, thereby enabling good printing on uncoated tablets. Further, it was confirmed that the rate of defective printing on the tablets printed on with the inks for inkjet printers of Examples 1 to 7 was small, and that good printing was therefore ensured.

Further, the dry-ink films of the tablets printed with the inks for inkjet printers of Examples 1 to 7 have a superior hardness, i.e., HB or 2B. Further, the tablets in Examples 8 to 21 did not have smudges or detachment of the printed characters, or smudges due to the printed characters on a tablet transferring onto another tablet. This is presumably because of the large content of shellac contained as a resin of the ink for inkjet printers, and the small content of the carbon powder pigment as a pigment of the ink for inkjet printers.

In contrast, when the printing was performed using the inks for inkjet printers of Comparative Examples 1 to 3, the hardness of the dry-ink film was low, i.e., 6B. In the tablets of Comparative Examples 4 to 6, and the tablets of Comparative Examples 8 to 10, the smudges due to transfer of the printed characters on a tablet onto another tablets were observed. In the tablets of Comparative Examples 5 and 6, and Comparative Examples 8 to 10, detachment and smudges of the printed characters were observed.

Further, in Comparative Example 7, since the proportion of the powder in the tablet surface was large, i.e., 0.3 wt %, the legibility was low despite the high hardness (HB) of the dry-ink film, and detachment of the printed dots was observed. However, Comparative Example 7 was satisfactory in terms of transfer of the smudges.

As another example of ink, for a formulation containing 2 wt % of pigment and 20 wt % of resin, which is 10 times the resin, the hardness of the dry-ink film was HB, which was within the appropriate tablet hardness range, thereby obtaining an ink with high blackness. However, since its viscosity greatly exceeded the adequate viscosity for a continuous inkjet printer, there was difficulty in discharge stability.

Further, for an ink obtained by fusing Food Red No. 3 in wax, oil, and propylene glycol, the pencil hardness of the dry film was softer than 6B, and therefore smudges due to rubbing more easily occurred.

The invention claimed is:

1. A printed tablet consisting of an unprinted tablet, and a dry-ink film having a pencil hardness of 2B to 4H which is adhered to the surface of the unprinted tablet,
   an amount of powder in the surface of the unprinted tablet being 0.2 wt % or less based on the total weight of the unprinted tablet;
   wherein the dry-ink film comprises an ink containing a resin and a pigment, the amount of the resin being 15 to 50 parts by weight per part by weight of the pigment, the resin containing shellac, the pigment containing a carbon powder pigment, and the ink containing 0.05 to 0.7 wt % of the pigment, 0.75 to 25 wt % of the resin, and 50 to 98 wt % of ethanol; and
   the dry-ink film having a reflection density of 0.1 to 0.3.

2. The printed tablet according to claim 1, wherein the unprinted tablet is an uncoated tablet.

3. The printed tablet according to claim 1, wherein the dry-ink film is a dry-ink film printed by using an inkjet printer.

4. The printed tablet according to claim 1, wherein the tablet is an orally disintegrating tablet.

* * * * *